United States Patent
Woodruff et al.

(10) Patent No.: US 12,161,498 B2
(45) Date of Patent: Dec. 10, 2024

(54) BASELINE RESTORATION TECHNIQUE FOR PHOTON COUNTING COMPUTED TOMOGRAPHY USING ACTIVE REFERENCE

(71) Applicant: Analog Devices, Inc., Wilmington, MA (US)

(72) Inventors: Matthew A. Woodruff, Medford, MA (US); Patrick S. Riehl, Lynnfield, MA (US)

(73) Assignee: Analog Devices, Inc., Wilmington, MA (US)

( * ) Notice: Subject to any disclaimer, the term of this patent is extended or adjusted under 35 U.S.C. 154(b) by 287 days.

(21) Appl. No.: 17/725,242

(22) Filed: Apr. 20, 2022

(65) Prior Publication Data

US 2022/0361833 A1 Nov. 17, 2022

Related U.S. Application Data

(60) Provisional application No. 63/187,329, filed on May 11, 2021.

(51) Int. Cl.
*A61B 6/00* (2024.01)
*A61B 6/03* (2006.01)
(Continued)

(52) U.S. Cl.
CPC ............ *A61B 6/5205* (2013.01); *A61B 6/032* (2013.01); *A61B 6/4241* (2013.01); *G01T 1/247* (2013.01)

(58) Field of Classification Search
CPC ..... A61B 6/5205; A61B 6/032; A61B 6/4241; G01T 1/247; G01T 1/17
See application file for complete search history.

(56) References Cited

U.S. PATENT DOCUMENTS 7,863,578 B2  1/2011 Brenner et al.
8,384,038 B2  2/2013 Guo et al.
(Continued)

FOREIGN PATENT DOCUMENTS

CN  103685991 B  10/2017
CN  113661381 A  11/2021
(Continued)

OTHER PUBLICATIONS

English Abstract of CN103685991B, 1 page.
(Continued)

*Primary Examiner* — David P Porta
*Assistant Examiner* — Gisselle M Gutierrez
(74) *Attorney, Agent, or Firm* — ARENTFOX SCHIFF LLP

(57) ABSTRACT

One embodiment is circuitry for implementing a baseline restoration ("BLR") circuit for a photon-counting computed tomography ("PCCT") signal chain, the circuitry comprising a multi-level discriminator circuit for receiving a shaper voltage from the PCCT signal chain, the discriminator circuit outputting a digital signal indicative of one of a range of voltages within which the shaper voltage falls; a digital-to-analog converter ("DAC") connected to receive the digital signal output from the discriminator circuit, the DAC converting the received digital signal to a corresponding active reference voltage; and a feedback circuit that injects a cancellation current proportional to the difference between the shaper voltage and the active reference voltage at the input of the PCCT signal chain.

20 Claims, 13 Drawing Sheets

(51) Int. Cl.
  *A61B 6/42*    (2024.01)
  *G01T 1/24*    (2006.01)

(56) References Cited

U.S. PATENT DOCUMENTS

| | | |
|---|---|---|
| 8,941,076 B2 | 1/2015 | Abraham |
| 9,176,238 B2 | 11/2015 | Herrmann |
| 9,268,035 B2 | 2/2016 | Herrmann |
| 9,759,822 B2 | 9/2017 | Daerr et al. |
| 10,162,066 B2 | 12/2018 | Fu et al. |
| 2005/0228291 A1 | 10/2005 | Chance |
| 2006/0015290 A1 | 1/2006 | Warburton et al. |
| 2008/0025385 A1 | 1/2008 | Barat et al. |
| 2015/0185332 A1 | 7/2015 | Herrmann |
| 2015/0327827 A1 | 11/2015 | Teshigawara |
| 2016/0170039 A1 | 6/2016 | Proksa |
| 2016/0377745 A1* | 12/2016 | Daerr ............... G01T 1/247 250/371 |
| 2021/0382188 A1 | 12/2021 | Steadman Booker et al. |
| 2021/0401387 A1 | 12/2021 | Hupfer et al. |
| 2023/0228888 A1* | 7/2023 | Riehl ............... G01T 1/17 378/5 |
| 2023/0367025 A1* | 11/2023 | Riehl ............... G01N 23/046 |

FOREIGN PATENT DOCUMENTS

| | | |
|---|---|---|
| EP | 2049917 B1 | 4/2015 |
| EP | 3074791 B1 | 6/2019 |

OTHER PUBLICATIONS

International Search Report and Written Opinion issued in PCT/US2023/079474 mailed Feb. 20, 2024, 16 pages.

R. Kleczek et al., "The design of low power low noise high speed CMOS readout front-end electronics for silicon Strip detectors," Mixed Design of Integrated Circuits and Systems (MIXDES), 2011 Proceedings of the 18th International Conference, IEEE, Jun. 16, 2011, pp. 374-378.

* cited by examiner

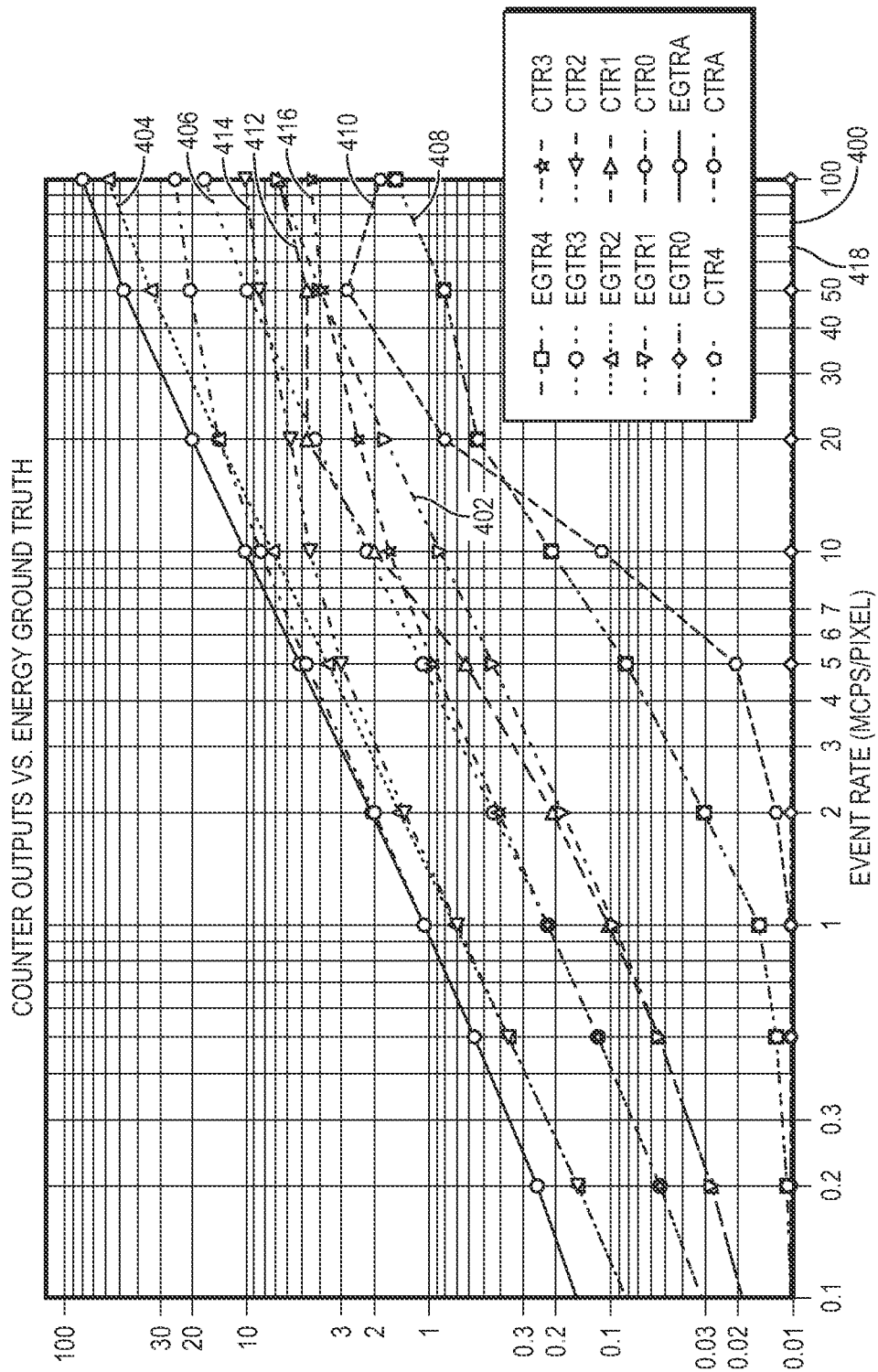

BASELINE RESTORATION TECHNIQUE FOR PHOTON COUNTING COMPUTED TOMOGRAPHY USING ACTIVE REFERENCE

CROSS-REFERENCE TO RELATED APPLICATION

This application claims the benefit of and priority to U.S. Patent Application Ser. No. 63/187,329, filed May 11, 2021, entitled "BASELINE RESTORATION TECHNIQUE FOR PHOTON COUNTING COMPUTED TOMOGRAPHY USING ACTIVE REFERENCE," which is incorporated herein by reference in its entirety.

FIELD OF THE DISCLOSURE

This disclosure relates generally to the field of photon counting computed tomography (PCCT) and, more particularly, to a baseline restoration (BLR) technique for PCCT using an active reference.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which:

FIG. 4 illustrates counting curves for the PCCT signal chain of FIG. 1 with BLR enabled;

DETAILED DESCRIPTION OF EXAMPLE EMBODIMENTS

Figure 1:
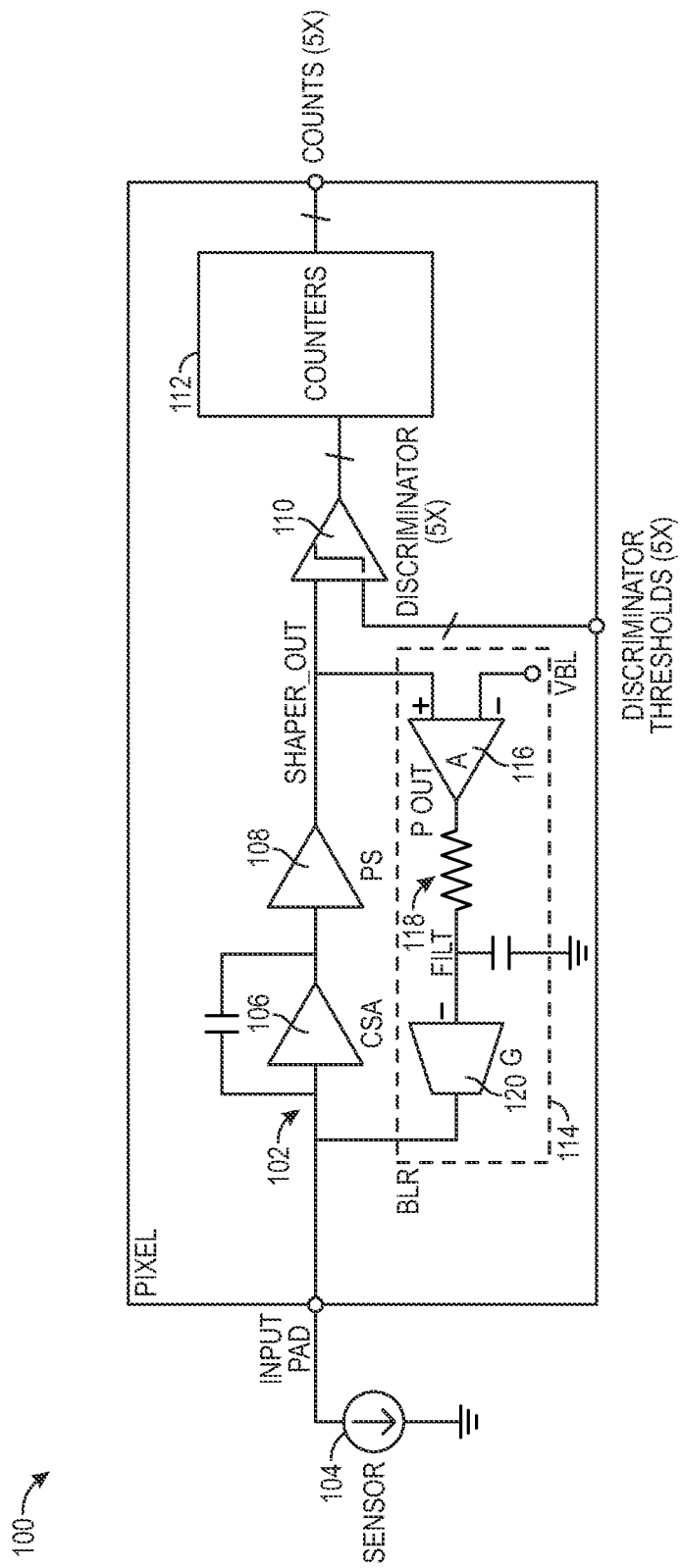
FIG. 1 is a schematic block diagram of a typical PCCT signal chain including a linear BLR circuit in accordance with certain embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B, and C). The term "between," when used with reference to measurement ranges, is inclusive of the ends of the measurement ranges. When used herein, the notation "A/B/C" means (A), (B), and/or (C).

The description uses the phrases "in an embodiment" or "in embodiments," which may each refer to one or more of the same or different embodiments. Furthermore, the terms "comprising," "including," "having," and the like, as used with respect to embodiments of the present disclosure, are synonymous. The disclosure may use perspective-based descriptions such as "above," "below," "top," "bottom," and "side"; such descriptions are used to facilitate the discussion and are not intended to restrict the application of disclosed embodiments. The accompanying drawings are not necessarily drawn to scale. Unless otherwise specified, the use of the ordinal adjectives "first," "second," and "third," etc., to describe a common object, merely indicate that different instances of like objects are being referred to and are not intended to imply that the objects so described must be in a given sequence, either temporally, spatially, in ranking or in any other manner.

In the following detailed description, reference is made to the accompanying drawings that form a part hereof, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense.

The following disclosure describes various illustrative embodiments and examples for implementing the features and functionality of the present disclosure. While particular components, arrangements, and/or features are described below in connection with various example embodiments, these are merely examples used to simplify the present disclosure and are not intended to be limiting. It will of course be appreciated that in the development of any actual embodiment, numerous implementation-specific decisions must be made to achieve the developer's specific goals, including compliance with system, business, and/or legal constraints, which may vary from one implementation to another. Moreover, it will be appreciated that, while such a development effort might be complex and time-consuming; it would nevertheless be a routine undertaking for those of ordinary skill in the art having the benefit of this disclosure.

In the Specification, reference may be made to the spatial relationships between various components and to the spatial orientation of various aspects of components as depicted in the attached drawings. However, as will be recognized by those skilled in the art after a complete reading of the present disclosure, the devices, components, members, apparatuses, etc. described herein may be positioned in any desired orientation. Thus, the use of terms such as "above", "below", "upper", "lower", "top", "bottom", or other similar terms to describe a spatial relationship between various components or to describe the spatial orientation of aspects of such components, should be understood to describe a relative relationship between the components or a spatial orientation of aspects of such components, respectively, as the components described herein may be oriented in any desired direction. When used to describe a range of dimensions or other characteristics (e.g., time, pressure, temperature, length, width, etc.) of an element, operations, and/or conditions, the phrase "between X and Y" represents a range that includes X and Y.

Further, the present disclosure may repeat reference numerals and/or letters in the various examples. This repetition is for the purpose of simplicity and clarity and does not in itself dictate a relationship between the various embodiments and/or configurations discussed. Example embodiments that may be used to implement the features and functionality of this disclosure will now be described with more particular reference to the accompanying FIGURES.

In a traditional computed tomography (CT) scanning system, X-rays generated by an X-ray source, passed through an object of interest, and are transformed by a scintillator into visible light that is captured by a detector implemented as a photodiode arrays. The photodiode arrays transform the light into analog electrical signals, which are converted into digital signals using an analog-to-digital (A/D) converter. The digital signal output from the A/D converter is used to produce a gray scale image referred to as a CT scan.

Photon-counting CT (PCCT) imaging is relatively new technique that may offer significant advantages and improvements over existing CT imaging techniques described above. A photon-counting CT system employs a photon-counting detector (PCD) comprising a semiconductor layer for implementing an array of detector pixels that register the interactions of individual photons with the PCD. By tracking the deposited energy of each interaction, detector pixels of a PCD record an approximate energy spectrum as well as luminous intensity, such that photon-counting CT is a spectral, or energy-resolved, CT technique. In contrast, traditional CT scanners use energy-integrating detectors (EIDs) in which the total energy from one or more photons as well as electronic noise deposited in a pixel during a fixed period of time is registered. EIDs therefore register only luminous intensity, analogous to black-and-white photography. In contrast, PCDs register both luminous intensity and spectral information, analogous to color photography.

Photon-counting CT imaging turns the three-step process described above into a more streamlined direct conversion from X-ray to charge via semiconductor layer comprising the PCD. In particular, the semiconductor material used to implement the PCD efficiently turns each X-ray photon into a burst of charge that is proportional to the energy of the X-ray. Benefits of this technology include improved signal-to-noise, reduced X-ray dose to the patient due to the higher contrast that may be achieved with the same X-ray dose, improved spatial resolution and, through use of several "energy bins," the ability to distinguish multiple contrast agents and multiple types of materials/tissues.

When a photon interacts in a PCD, the height of a resulting electrical pulse is approximately proportional to the energy of the photon. By comparing each pulse produced in a pixel with a suitable low-energy threshold, contributions from low-energy events (resulting from both photon interactions and electronic noise) can be filtered out. As a result, PCDs have higher signal-to-noise and contrast-to-noise ratios as compared to EIDs, enabling an increase in image quality at the same X-ray exposure level or a decrease in patient X-ray dose with the same image quality.

Introduction of more energy thresholds above the low-energy threshold enables a PCD to be divided into several discrete energy bins. Each registered photon is assigned to a specific bin depending on its energy, such that each pixel measures a histogram of the incident X-ray spectrum. This spectral information enables a qualitative determination of the material composition of each pixel in the reconstructed CT image, as opposed to the estimated average linear attenuation coefficient obtained in a conventional CT scan. Additionally, using more than two energy bins enables discrimination between dense bones and calcifications versus heavier elements commonly used as contrast agents, reducing the need for a reference scan before contrast injection and thereby further reducing the amount of X-ray dose to which a patient is subjected.

FIG. 1 is a schematic block diagram illustrating a system 100 for implementing a typical PCCT signal chain in accordance with embodiments described herein. A forward signal path 102 from a sensor 104 includes a charge-sensitive amplifier (CSA) 106 and pulse shaper (PS) 108, followed by a discriminator 110 and counters 112. X-rays impinging on the sensor 104 cause current pulses (or charge packets) to be injected to the forward signal path 102. The forward signal path 102 converts these current pulses to voltage pulses at the input of the discriminator 110. The discriminator 110 quantizes the current pulses according to energy, which are in turn counted by the counters 112. The sensor 104 also includes a significant component of slowly varying leakage current. Left uncompensated, this leakage current would pass through the forward signal chain and produce an offset at the discriminator 110 inputs, distorting the measured spectrum. To counter this effect, a baseline restorer (BLR) 114 is introduced. The BLR 114 creates a slow negative feedback loop around the CSA 106 and PS 108 that regulates the long-term value of the PS output to some desired voltage. It does this by injecting a slowly varying current at the CSA 106 input. The BLR circuit 114 includes a linear voltage gain stage 116 referenced to the desired baseline voltage Vbl. The voltage gain state 116 is followed by a low-pass filter 118 and finally a transconductor 120. If implemented with linear circuits, the BLR 114 will regulate the average shaper output voltage (shaper_out). If flux rates are low, meaning that if the input current due to X-ray flux is small compared to the leakage current, this is equivalent to regulating the baseline voltage of the shaper 108 output.

Figure 2A:
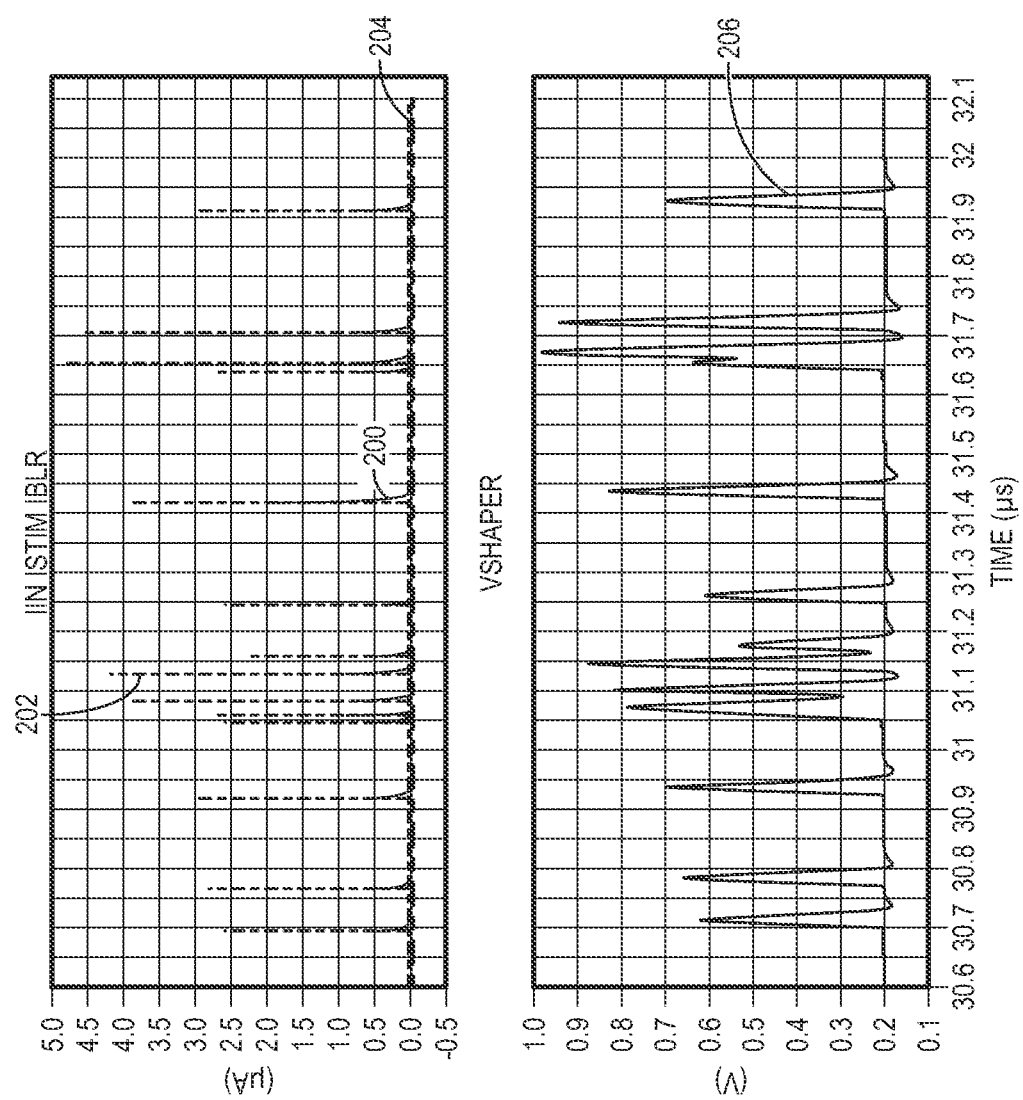
FIGS. 2A and 2B are graphs illustrating waveforms of the BLR of the PCCT of FIG. 1 during low X-ray flux.
Figure 2B:
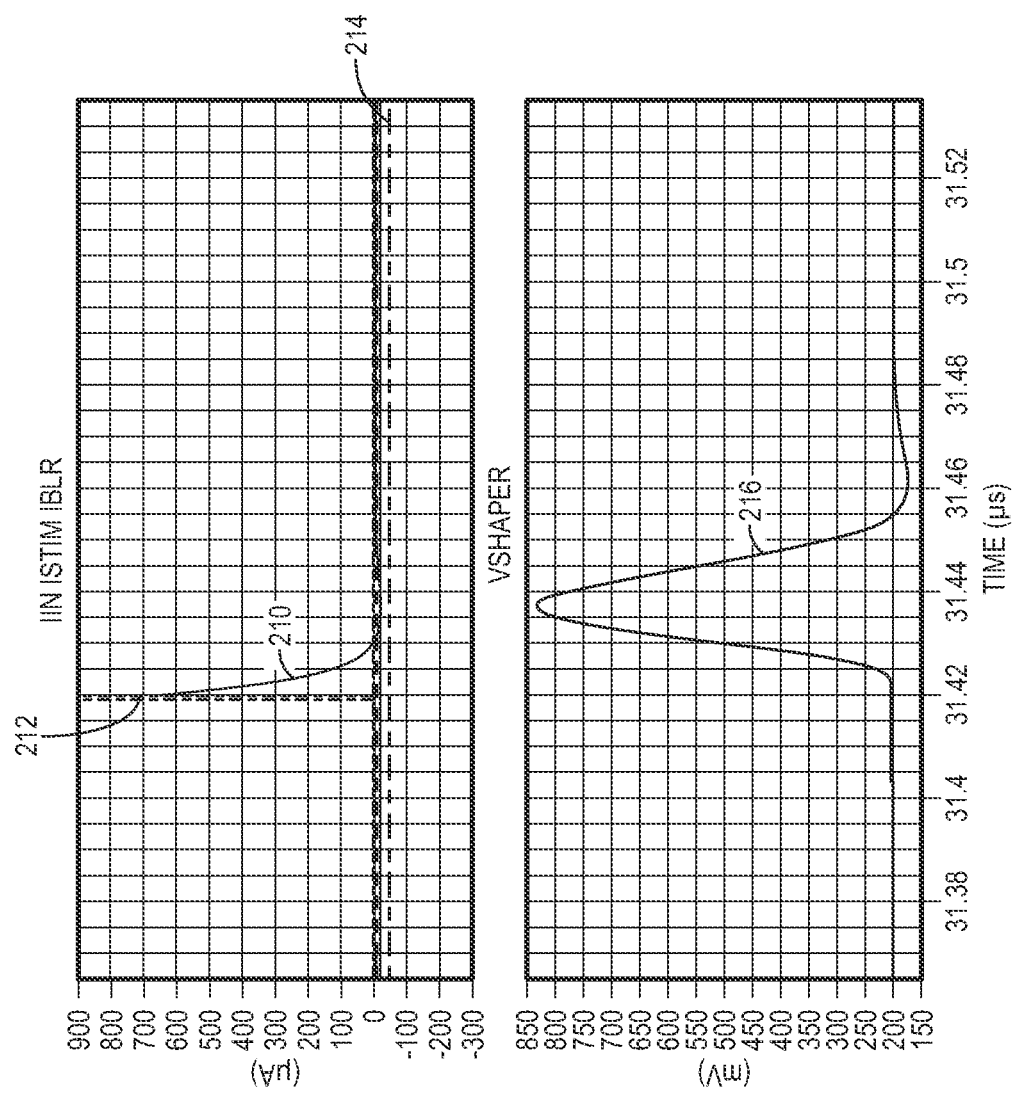

FIGS. 2A and 2B illustrate waveforms for a simple PCCT signal chain under low X-ray flux. In FIG. 2A, waveforms 200, 202, and 204, respectively correspond to an input current to the CSA (Iin), a stimulus current (Istim), and a BLR cancellation current (Iblr). Waveform 206 is a corresponding output voltage of the shaper (vshaper). Similarly, in FIG. 2B, waveforms 208, 210, and 212, respectively correspond to Iin, Istm, and Iblr, and waveform 214 is the corresponding vshaper. The plots of FIGS. 2A and 2B illustrate a family of stimuli with different values of leakage current from 35 nA to 5 nA. The BLR circuit regulates the average voltage of shaper output voltage (vshaper) to 200 mV in all cases. All of the shaper voltage curves are indistinguishable by eye and the baseline voltage settles at 200 mV, as desired.

An issue commonly referred to as "undershoot" occurs when the signal current due to X-ray flux is significant with respect to the leakage current. In particular, undershoot occurs when the average of the signal current Is high enough that its cancellation by the BLR circuit causes a significant negative shift in the baseline. BLR undershoot occurs because there is a net negative charge arriving at the input of the BLR circuit in the form of charge packets. In order to maintain the average shaper voltage constant (as in linear BLR), the BLR circuit must apply a steady positive current that exactly opposes the average signal current. During a gap between events, this positive current causes BLR undershoot.

Figure 3A:
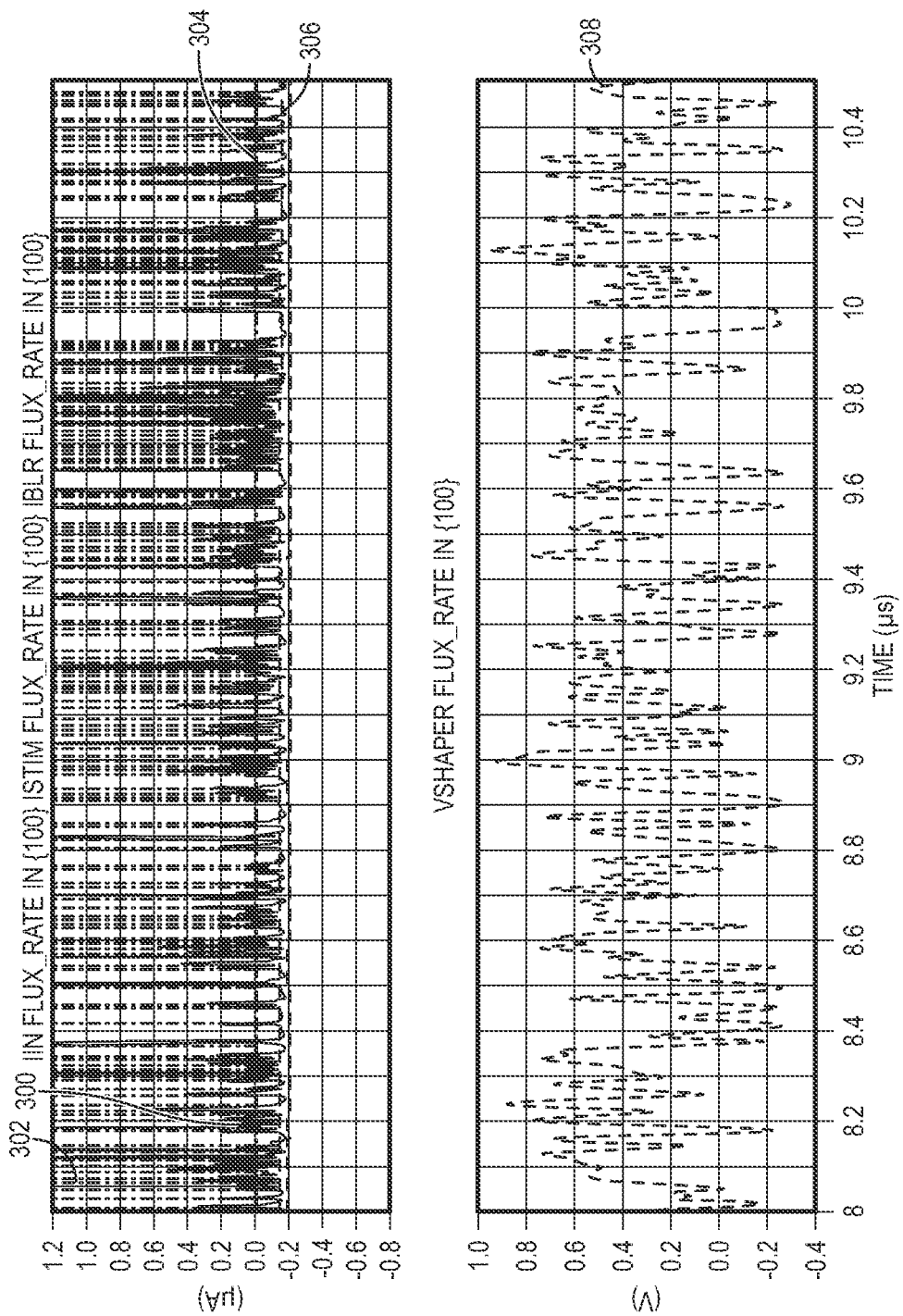
FIGS. 3A and 3B are graphs illustrating waveforms of the BLR of the PCCT of FIG. 1 during high X-ray flux.
Figure 3B:
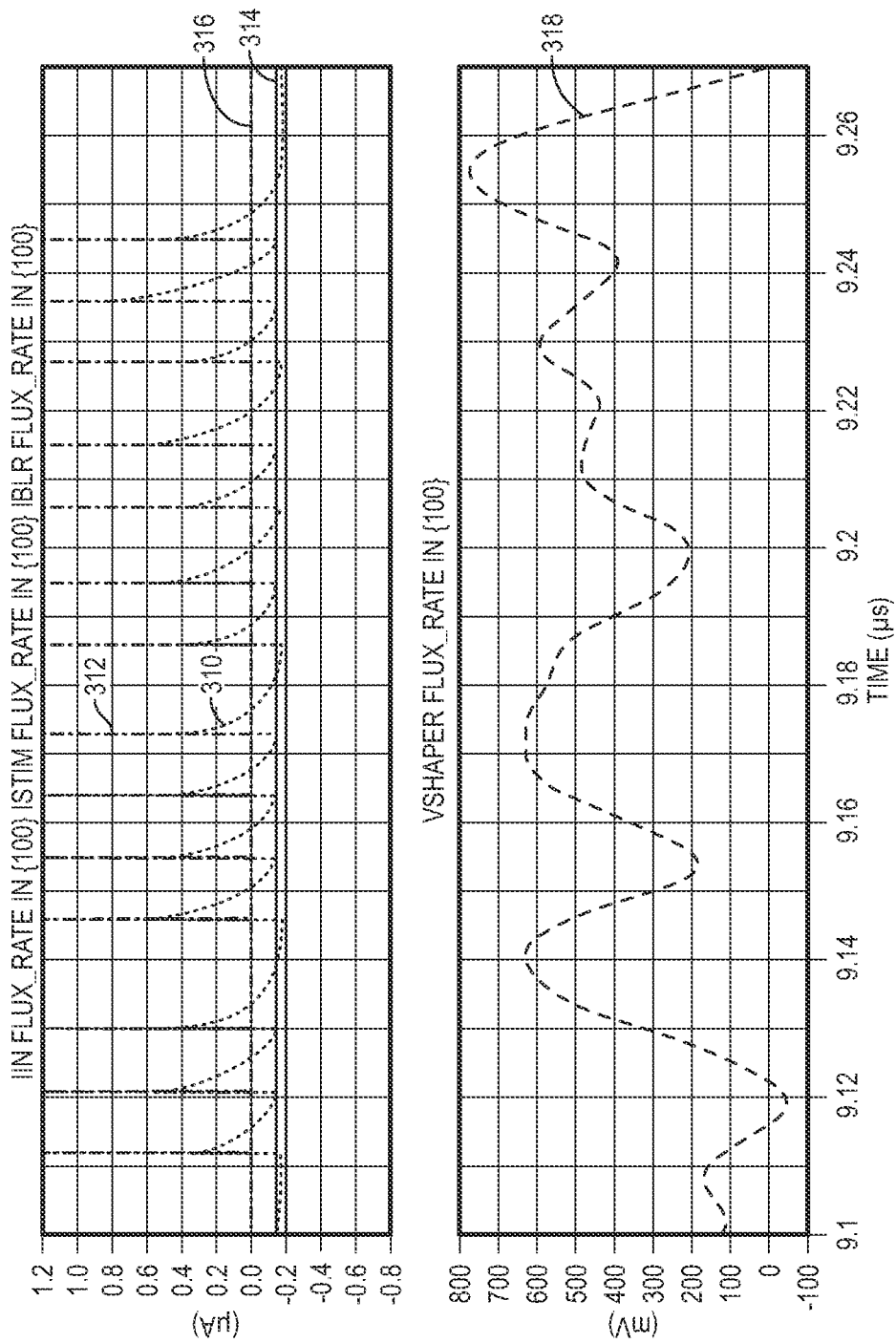

FIGS. 3A and 3B respectively illustrate waveforms 300-314 representing flux rates of the corresponding waveforms

200-214 shown in FIGS. 2A and 2B. As illustrated in FIGS. 3A and 3B, the BLR circuit cancels the leakage current successfully, as evidenced by the shaper output voltage (vshaper) curves lying on top of each other; however, the baseline of the shaper output voltage is significantly less than 200 mV, due to the fact that the average stimulus current (Istim) contains a significant contribution from signal current. The BLR circuit has no way to distinguish leakage current from signal current, so it cancels both. The resulting measured spectrum includes a shift to lower energies, as each charge pulse (if it can be distinguished from others) starts from a lowered baseline.

The effect of undershoot can be observed in FIG. 4, which illustrates the actual generated events per bin (i.e., "ground truth") in lines 400, 402, 404, 406, 408, and the corresponding counter outputs in lines 410, 412, 414, 416, 418, for each of the 5 counter bins for a typical frame of PCCT data. An increase in counts of approximately 1-2 mega counts per second (Mcps) relative to the ground truth may be observed in bins 0 and 1 (comparing line 400 to line 410 and line 402 to line 412), serving as evidence that undershoot causes higher energy events to be miscounted in lower energy bins.

Figure 5:
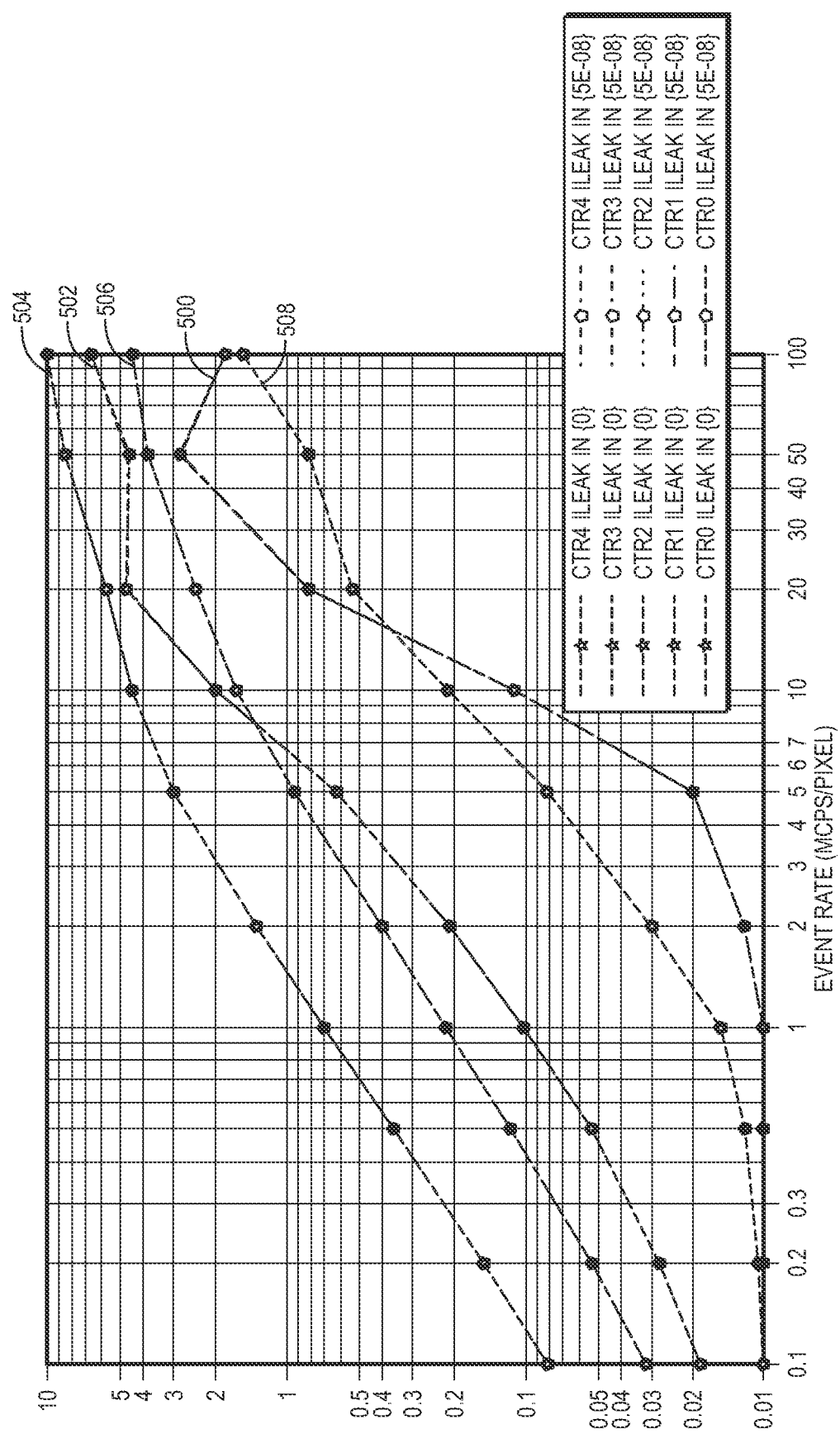
FIG. 5 illustrates a comparison of counting curves for the PCCT signal chain of FIG. 1 with BLR for 0 nA leakage and 50 nA leakage.

Waveforms 500, 502, 504, 506, 508 shown in FIG. 5 illustrate the effectiveness of the BLR in canceling leakage currents. As shown in FIG. 5, there is negligible difference between the counting results with 50 nA leakage current and the counting results with a 0 nA leakage current; the undershoot effect is effectively the same for both cases.

Figure 6:
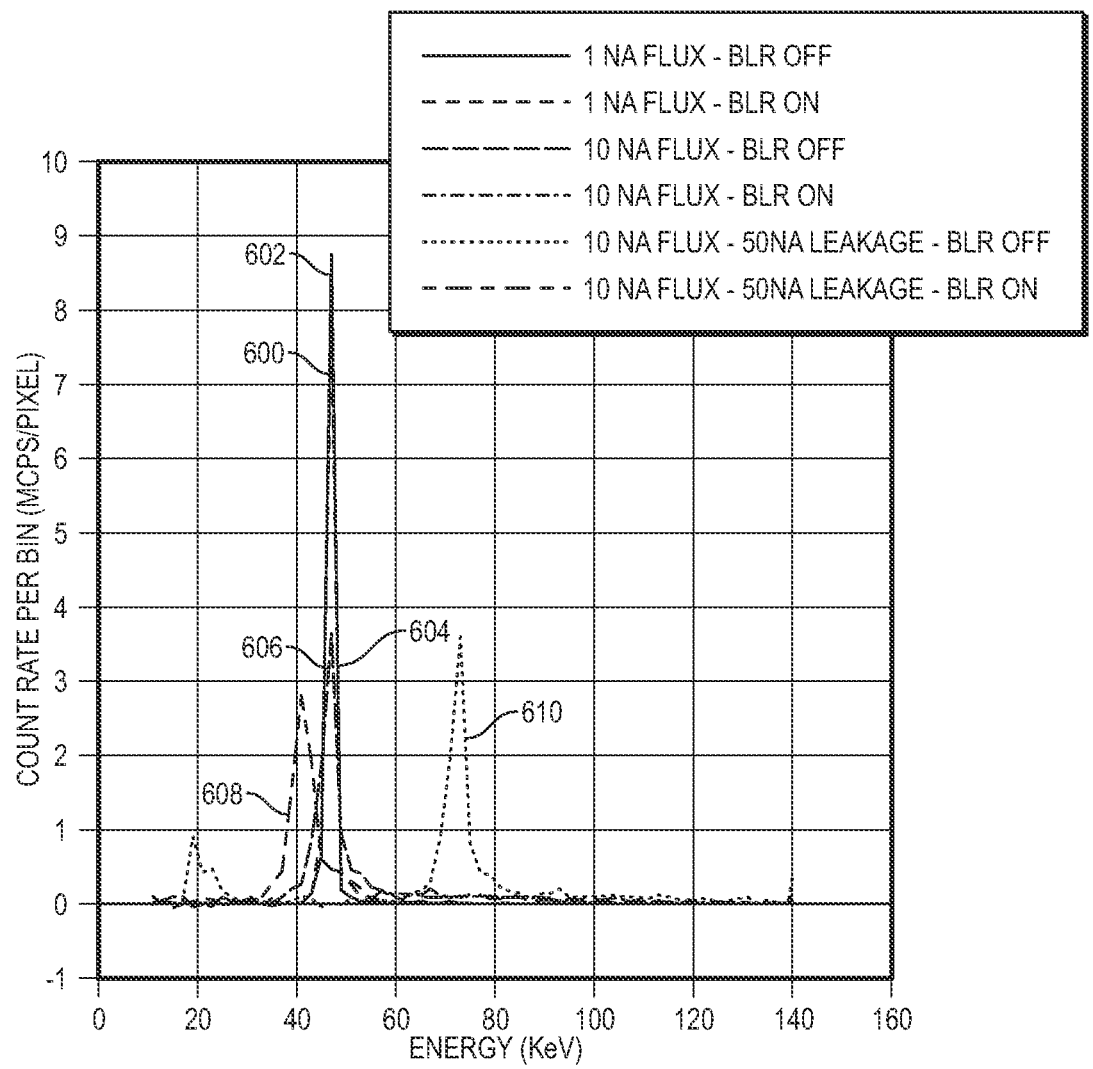
FIG. 6 illustrates results of an experiment illustrating the undershoot effect of the BLR of the PCCT of FIG. 1.

Waveforms 600, 602, 604, 606, 608, 610, shown in FIG. 6 illustrate the results of another experiment demonstrating the BLR undershoot effect. In particular, the waveforms 600-610 shown in FIG. 6 are the result of a series of simulations carried out with a superposition of a 10 Mcps, 50 kiloelectron volt (keV) periodic tone with a realistic spectrum at varying flux rates. The output spectrum was captured using a threshold sweep. The spectrum flux was kept at a low level so that the tone could be clearly seen in the output spectrum. With 1 nA flux, there is no observable difference in the spectrum whether the BLR is on (waveform 600) or off (waveform 602). With 10 nA flux, a shift to lower energy occurs in the observed tone when the BLR is on, as evidenced by the location of the peak of waveform 608. The tone does not shift with the BLR off. Once a leakage current is applied, the tone shifts dramatically higher with BLR off (waveform 610), while it remains at the same energy level with BLR on (waveform 608). This result is summarized in TABLE 1 below.

TABLE 1

|         | 0 nA leakage | 50 nA leakage |
|---------|--------------|---------------|
| BLR off | 47 keV       | 73 keV        |
| BLR on  | 41 keV       | 41 keV        |

Although undershoot is undesirable, the benefits of using a BLR to cancel leakage current heavily outweigh the costs. The undershoot effect is a response to flux changes, which are deterministic. There is an opportunity to correct for this in post-processing. The leakage current can vary over many frames even as flux remains constant. Moreover, the leakage current may vary from pixel to pixel or with aging or temperature of the sensor. Accordingly, it is much more important to cancel the leakage current than to avoid the undershoot effect. Use of a BLR loop is desirable, therefore, and the BLR loop must have sufficient loop gain to cancel most of the leakage current.

What is needed is a way to suppress the response of the BLR circuit during signal events without affecting either the forward signal path or accurate control of the baseline voltage during periods of low signal activity. In a conventional method, the pulse shaper voltage is compared to a reference voltage set to the desired baseline voltage. A feedback loop forces the shaper voltage equal to the reference voltage if no signal current is present. During signal events, however, the feedback loop integrates the positive signal, creating a negative offset on the shaper voltage.

In accordance with features of embodiments described herein, discriminator outputs are used as a digital signal driving a digital-to-analog converter (DAC) with a specific transfer function that models the detected pulse shape. The DAC outputs a voltage equal to the highest discriminator threshold exceeded. The resulting DAC output is a heavily quantized, continuous-time waveform that roughly tracks the pulse shaper voltage. This relieves the BLR circuit from having to cancel signal charge and allows it to focus on canceling leakage current as intended.

Figure 7:
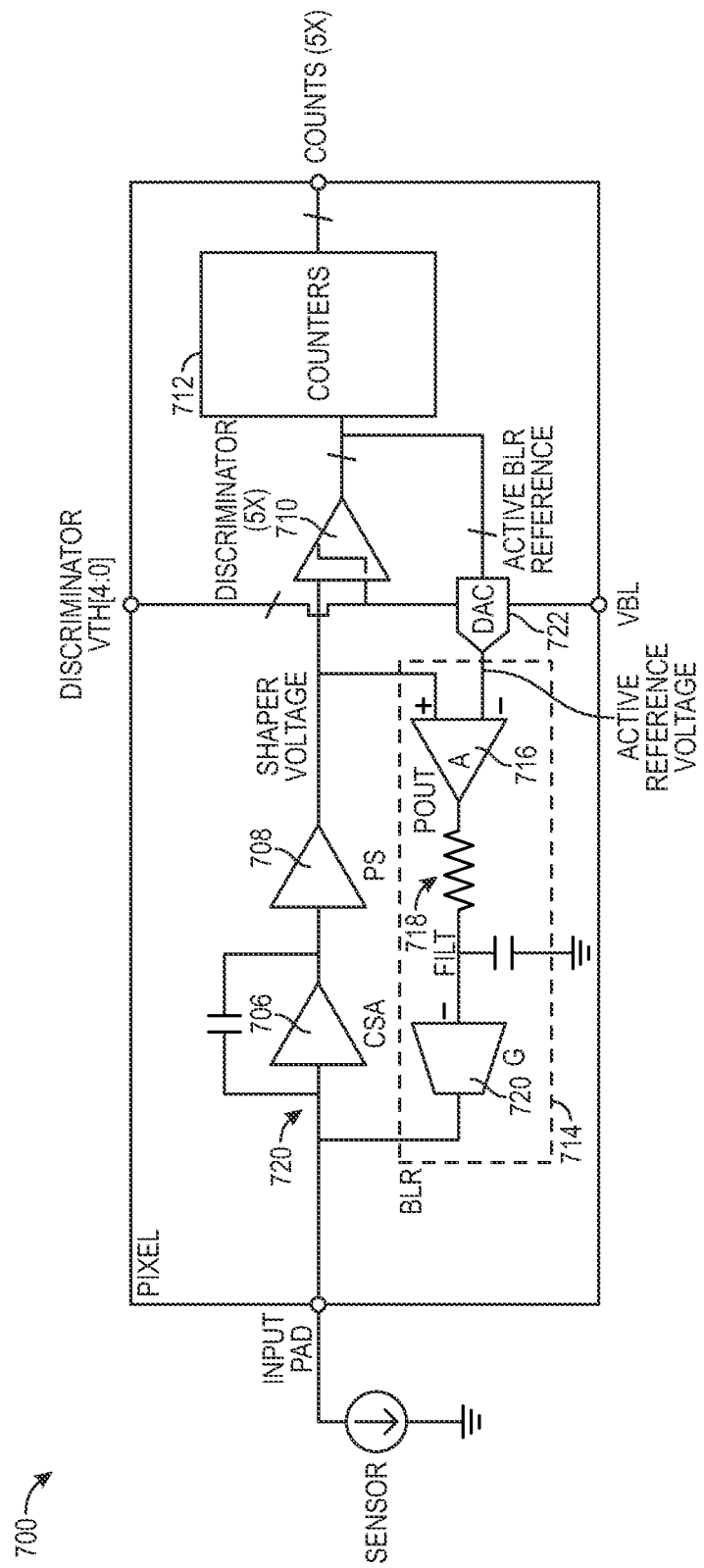
FIG. 7 is a schematic block diagram illustrating a system for implementing an active reference for a BLR circuit in accordance with embodiments described herein.

FIG. 7 is a schematic block diagram illustrating a system 700 for implementing an active reference for a BLR circuit in accordance with embodiments described herein. Similar to the system 100 (FIG. 1), in system 700, a forward signal path 702 from a sensor 704 includes a charge-sensitive amplifier (CSA) 706 and pulse shaper (PS) 708, followed by a discriminator 710 and counters 712. X-rays impinging on the sensor 704 cause current pulses (or charge packets) to be injected to the forward signal path 702. The forward signal path 702 converts these current pulses to voltage pulses at the input of the discriminator 710. The discriminator 710 quantizes the current pulses according to energy, which are in turn counted by the counters 712. For reasons described in detail above, the system 700 includes a BLR 714, which (as also described above) creates a slow negative feedback loop around the CSA 706 and PS 708 that regulates the long-term value of the PS output to some desired voltage. It does this by injecting a slowly varying current at the CSA 706 input. The BLR circuit 714 includes a linear voltage gain stage 716 followed by a low-pass filter 718 and a transconductor 720. In accordance with features of embodiments described herein, instead of being referenced to a static baseline voltage Vbl, the voltage gain state 716 is referenced to a dynamic/active reference output from a digital-to-analog converter (DAC) 722, the input of which is tied to the output of the discriminator 710. As noted above, DAC 722 implements a transfer function that models the detected pulse shape. In particular, the DAC 722 outputs a voltage equal to the highest discriminator threshold exceeded.

It will be recognized that the feedback from the BLR circuit could be applied to the input of the PCCT signal chain as shown, or it could be applied to an intermediate node, such as the output of the CSA 106.

It will be recognized that the BLR 714 can be modified to function as a delta modulator by replacing the linear gain stage 716 with a comparator. In this configuration, the low-pass filter 718 acts as the integrator in the delta modulator.

Figure 8:
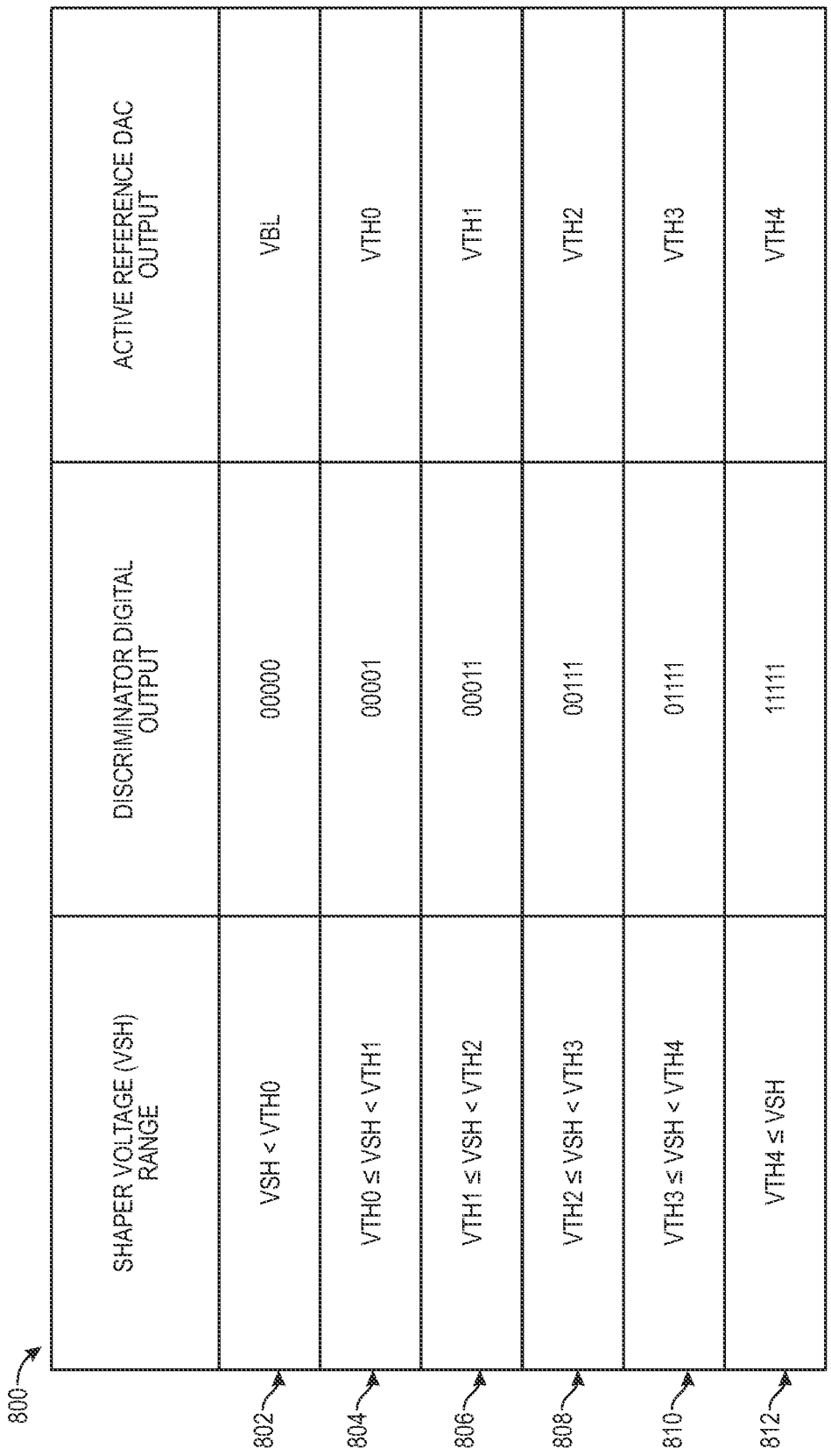
FIG. 8 is a chart illustrating example active reference signals output from a digital-to-analog circuit (DAC) for designated shaper voltage (Vsh) ranges, each of which corresponds to a digital output of an example 5-level discriminator, in connection with the example system illustrated in FIG. 7.

FIG. 8 is a chart 800 illustrating example active reference signals output from the DAC 710 for designated shaper voltage (Vsh) ranges, each of which corresponds to a digital output of an example 5-level discriminator. For example, referring to line 802, for Vsh less than a first threshold voltage Vth0, the discriminator output will be 00000 and the active reference signal input to the gain stage from the DAC will be equal to the desired baseline voltage Vbl. Referring to line 804, for Vsh greater than or equal to Vth0 and less than a second threshold voltage Vth1, the discriminator output will be 00001 and the active reference signal output to the gain stage from the DAC will be Vth0. Referring to line 806, for Vsh greater than or equal to Vth1 and less than a third reference voltage Vth2, the discriminator output will be 00011 and the active reference signal input to the gain stage from the DAC will be Vth1. Referring to line 808, for Vsh greater than or equal to Vth2 and less than a fourth reference voltage Vth3, the discriminator output will be 00111 and the active reference signal input to the gain stage from the DAC will be Vth2. Referring to line 810, for Vsh greater than or equal to Vth3 and less than a firth threshold voltage Vth4, the discriminator output will be 01111 and the active reference signal input to the gain stage from the DAC will be Vth3. Finally, referring to line 812, for Vsh greater than or equal to Vth4, the discriminator output will be 11111 and the active reference signal input to the gain stage from the DAC will be Vth4.

As noted above, the example depicted in FIG. 8 is for a five-level discriminator; however, the techniques described herein could be extended to more or fewer levels as desired without departing from the spirit or scope of the teachings. Vth[0:4] are the discriminator levels to which the shaper voltage Vsh is compared on the forward signal path. Vbl is the desired baseline voltage. The DAC outputs one of Vbl, Vth[0:4] depending on the instantaneous discriminator digital output.

The resulting DAC output is a heavily quantized, continuous-time waveform that roughly tracks the pulse shaper voltage. This relieves the BLR circuit from having to cancel signal charge and allows it to focus on canceling leakage current as intended.

Figure 9:
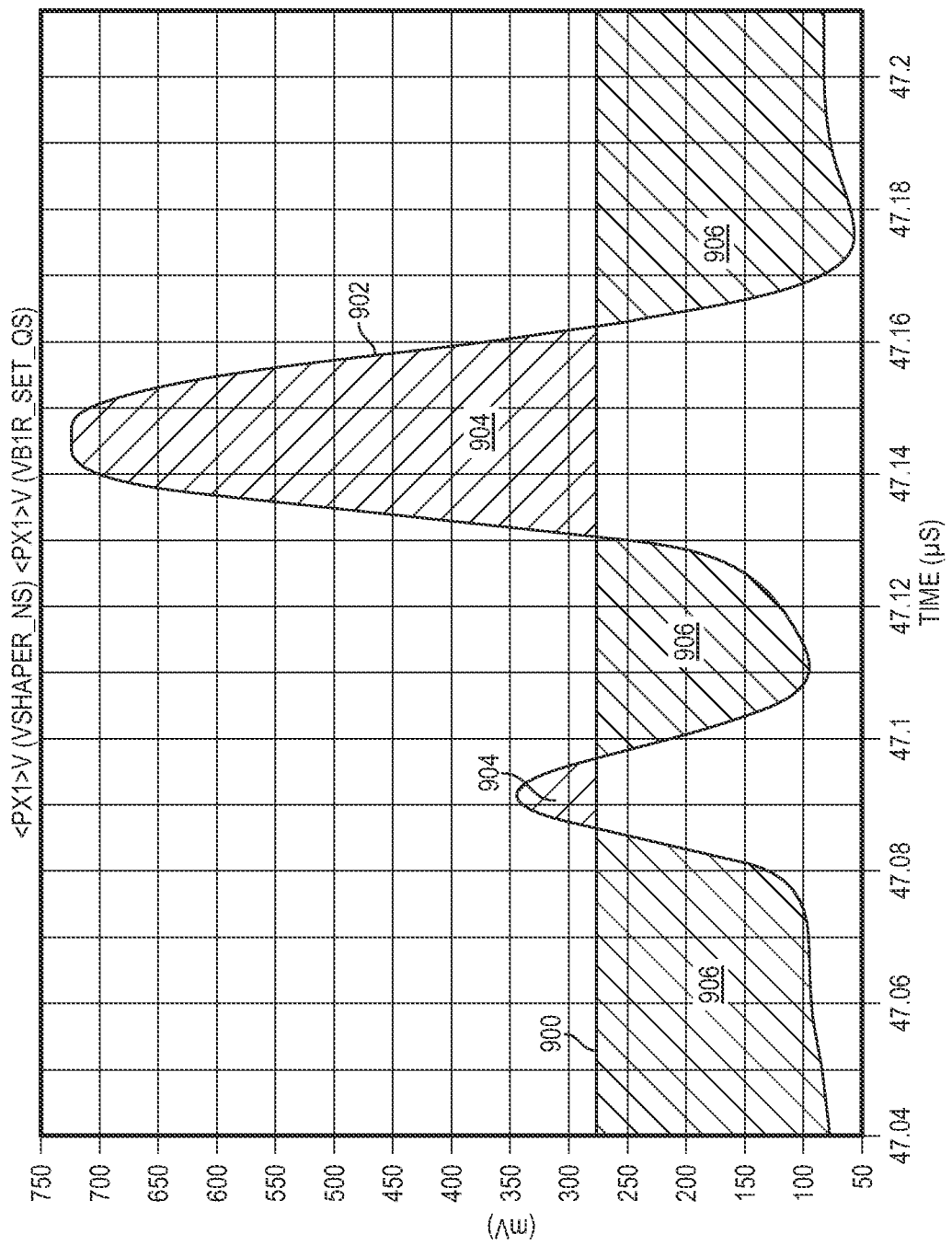
FIGS. 9 and 10 respectively illustrate graphs of waveforms in connection with a conventional BLR circuit, in which a static reference is deployed and waveforms in connection with a BLR circuit in accordance with embodiments described herein in which a dynamic reference is deployed.
Figure 10:
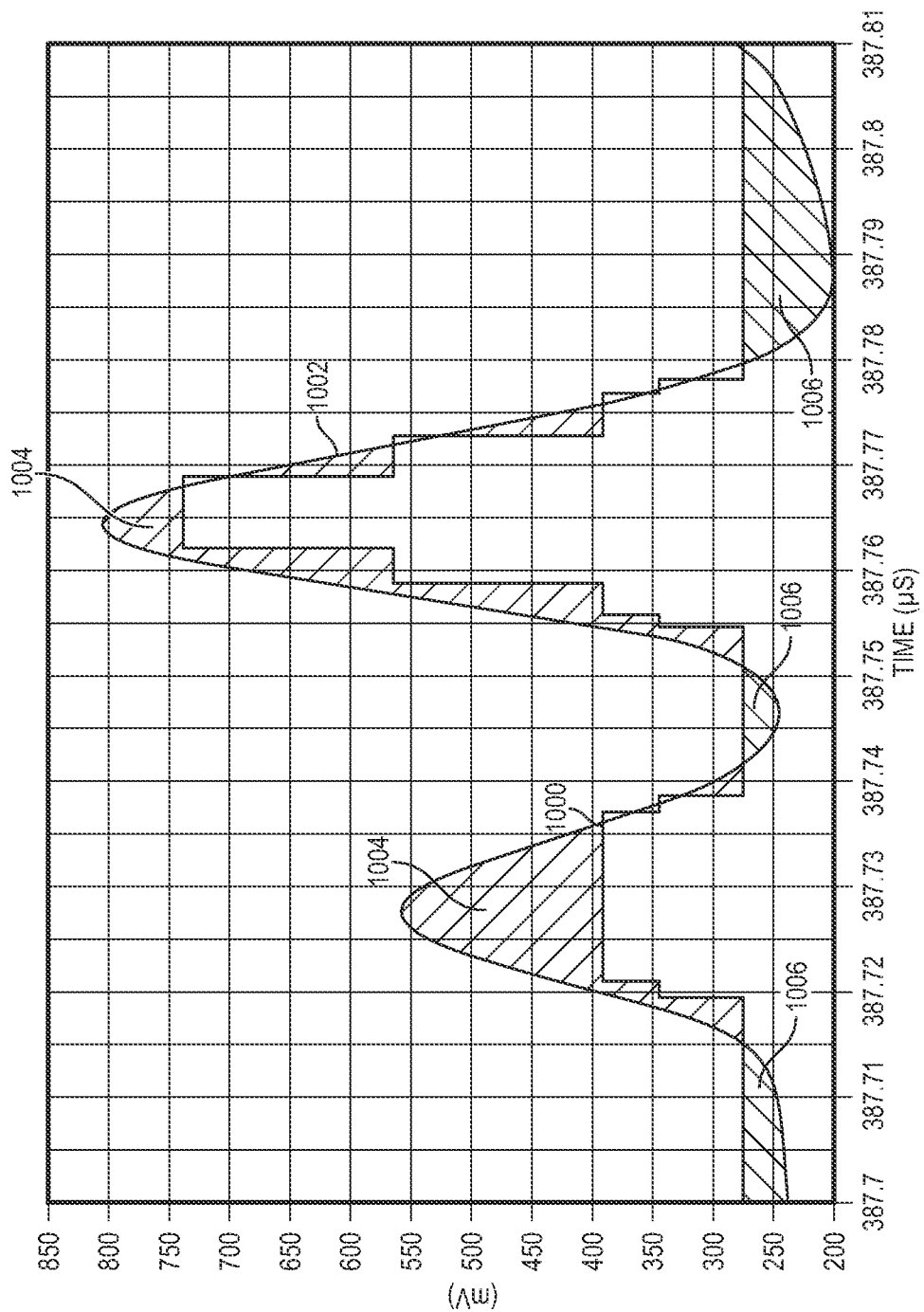

FIGS. 9 and 10 illustrate the waveforms in connection with a conventional BLR circuit, in which a static reference is deployed (such as illustrated in FIG. 1) and a BLR circuit in accordance with embodiments described herein in which a dynamic reference is deployed (such as illustrated in FIG. 7). In particular, in FIG. 9, a waveform 900 depicts a static reference signal and a waveform 902 depicts a shaper voltage signal. In FIG. 10, a waveform 1000 depicts a dynamic reference signal generated in accordance with embodiments described herein and a waveform 1002 depicts a shaper voltage signal. A BLR circuit in equilibrium will guarantee that the integral of the difference between the shaper voltage (Vsh) and the reference voltage (Vref) is zero. In graphical terms, this means that the area under the curve defined by Vsh minus Vref will have as much negative area (Vsh<Vref, corresponding to areas 904) as positive area (Vsh>Vref, corresponding to areas 906). In FIG. 9, the large positive peak of Vsh accumulates a large positive area. In order to balance this with an equal negative area, Vsh must be shifted negative with respect to Vref. In FIG. 10, the dynamic reference reduces the positive area accumulated by Vsh minus Vref. As a result, Vsh does not need to be shifted as much to balance the positive areas (including areas 1004) and negative areas (including areas 1006) of Vsh minus Vref. Thus, as illustrated in FIGS. 9 and 10, as compared to the conventional method in which a static reference is employed (FIG. 9) the BLR circuit of embodiments described herein in which a dynamic reference voltage is employed integrates much less of the signal events, thereby reducing baseline undershoot.

Figure 11:
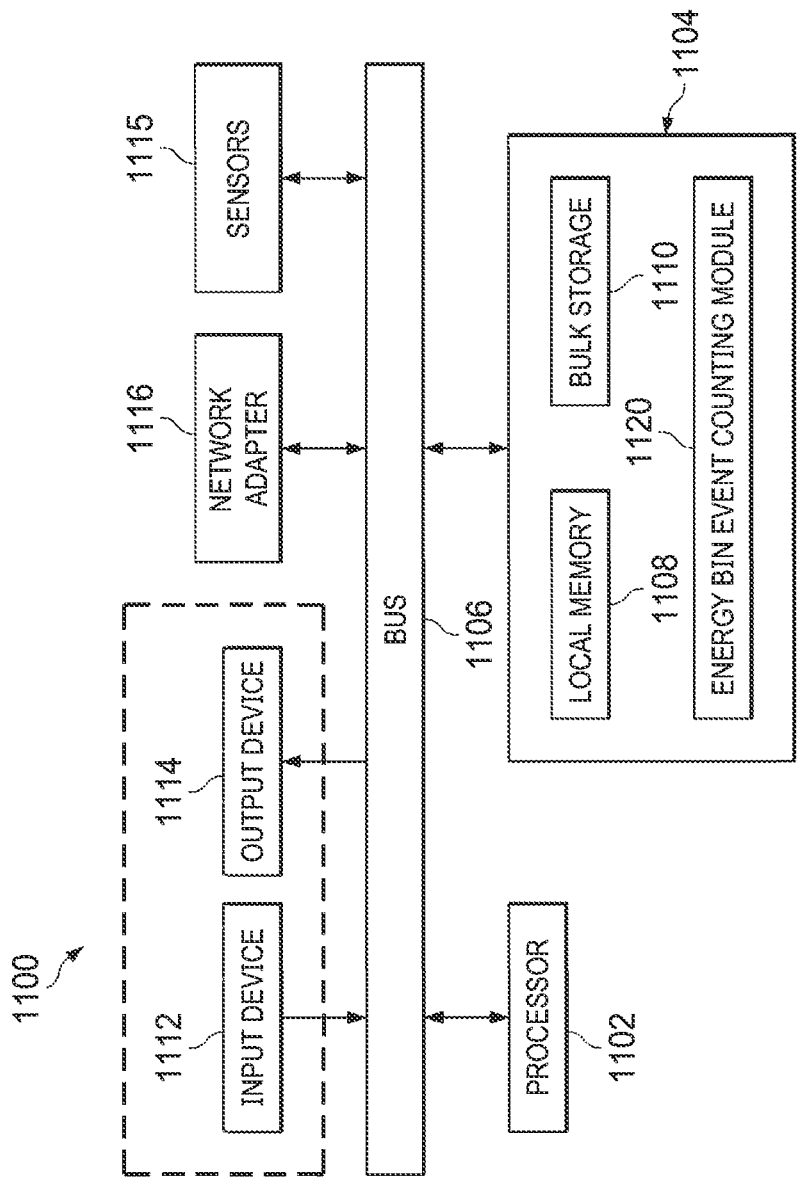
FIG. 11 is a block diagram of a computer system that may be used to implement all or some portion of a PCCT scanning system in accordance with features of certain embodiments described herein.

FIG. 11 is a block diagram illustrating an example system 1100 that may be configured to implement at least portions of techniques in accordance with embodiments described herein, and more particularly as shown in the FIGURES described hereinabove. As shown in FIG. 11, the system 1100 may include at least one processor 1102, e.g., a hardware processor 1102, coupled to memory elements 1104 through a system bus 1106. As such, the system may store program code and/or data within memory elements 1104. Further, the processor 1102 may execute the program code accessed from the memory elements 1104 via a system bus 1106. In one aspect, the system may be implemented as a computer that is suitable for storing and/or executing program code. It should be appreciated, however, that the system 1100 may be implemented in the form of any system including a processor and a memory that is capable of performing the functions described in this disclosure.

In some embodiments, the processor 1102 can execute software or an algorithm to perform the activities as discussed in this specification; in particular, activities related to embodiments described herein. The processor 1102 may include any combination of hardware, software, or firmware providing programmable logic, including by way of non-limiting example a microprocessor, a DSP, a field-programmable gate array (FPGA), a programmable logic array (PLA), an integrated circuit (IC), an application specific IC (ASIC), or a virtual machine processor. The processor 1102 may be communicatively coupled to the memory element 1104, for example in a direct-memory access (DMA) configuration, so that the processor 1102 may read from or write to the memory elements 1104.

In general, the memory elements 1104 may include any suitable volatile or non-volatile memory technology, including double data rate (DDR) random access memory (RAM), synchronous RAM (SRAM), dynamic RAM (DRAM), flash, read-only memory (ROM), optical media, virtual memory regions, magnetic or tape memory, or any other suitable technology. Unless specified otherwise, any of the memory elements discussed herein should be construed as being encompassed within the broad term "memory." The information being measured, processed, tracked or sent to or from any of the components of the system 1100 could be provided in any database, register, control list, cache, or storage structure, all of which can be referenced at any suitable timeframe. Any such storage options may be included within the broad term "memory" as used herein. Similarly, any of the potential processing elements, modules, and machines described herein should be construed as being encompassed within the broad term "processor." Each of the elements shown in the present figures may also include suitable interfaces for receiving, transmitting, and/or otherwise communicating data or information in a network environment so that they can communicate with, for example, a system having hardware similar or identical to another one of these elements.

In certain example implementations, mechanisms for implementing embodiments as outlined herein may be implemented by logic encoded in one or more tangible media, which may be inclusive of non-transitory media, e.g., embedded logic provided in an ASIC, in DSP instructions, software (potentially inclusive of object code and source code) to be executed by a processor, or other similar machine, etc. In some of these instances, memory elements, such as e.g., the memory elements 1104 shown in FIG. 11 can store data or information used for the operations described herein. This includes the memory elements being able to store software, logic, code, or processor instructions that are executed to carry out the activities described herein. A processor can execute any type of instructions associated with the data or information to achieve the operations detailed herein. In one example, the processors, such as e.g., the processor 1102 shown in FIG. 11, could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., an FPGA, a DSP, an erasable programmable read-only memory (EPROM), an electrically erasable programmable read-only memory (EEPROM)) or an ASIC that includes digital logic, software, code, electronic instructions, or any suitable combination thereof.

The memory elements 1104 may include one or more physical memory devices such as, for example, local memory 1108 and one or more bulk storage devices 1110. The local memory may refer to RAM or other non-persistent memory device(s) generally used during actual execution of the program code. A bulk storage device may be implemented as a hard drive or other persistent data storage device. The processing system 1100 may also include one or more cache memories (not shown) that provide temporary storage of at least some program code in order to reduce the number of times program code must be retrieved from the bulk storage device 1110 during execution.

As shown in FIG. 11, the memory elements 1104 may store an energy bin event counting module 1120. In various embodiments, the module 1120 may be stored in the local memory 1108, the one or more bulk storage devices 1110, or apart from the local memory and the bulk storage devices. It should be appreciated that the system 1100 may further execute an operating system (not shown in FIG. 11) that can facilitate execution of the module 1120. The module 1120, being implemented in the form of executable program code and/or data, can be read from, written to, and/or executed by the system 1100, e.g., by the processor 1102. Responsive to reading from, writing to, and/or executing the module 1120, the system 1100 may be configured to perform one or more operations or method steps described herein.

Input/output (I/O) devices depicted as an input device 1112 and an output device 1114, optionally, may be coupled to the system. Examples of input devices may include, but are not limited to, a keyboard, a pointing device such as a mouse, or the like. Examples of output devices may include, but are not limited to, a monitor or a display, speakers, or the like. In some implementations, the system may include a device driver (not shown) for the output device 1114. Input and/or output devices 1112, 1114 may be coupled to the system 1100 either directly or through intervening I/O controllers. Additionally, sensors 1115, may be coupled to the system 1100 either directly or through intervening controllers and/or drivers.

In an embodiment, the input and the output devices may be implemented as a combined input/output device (illustrated in FIG. 11 with a dashed line surrounding the input device 1112 and the output device 1114). An example of such a combined device is a touch sensitive display, also sometimes referred to as a "touch screen display" or simply "touch screen." In such an embodiment, input to the device may be provided by a movement of a physical object, such as e.g., a stylus or a finger of a user, on or near the touch screen display.

A network adapter 1116 may also, optionally, be coupled to the system 1100 to enable it to become coupled to other systems, computer systems, remote network devices, and/or remote storage devices through intervening private or public networks. The network adapter may comprise a data receiver for receiving data that is transmitted by said systems, devices and/or networks to the system 1100, and a data transmitter for transmitting data from the system 1100 to said systems, devices and/or networks. Modems, cable modems, and Ethernet cards are examples of different types of network adapter that may be used with the system 1100.

Example 1 provides circuitry for implementing a baseline restoration ("BLR") circuit for a photon-counting computed tomography ("PCCT") signal chain, the circuitry comprising a multi-level discriminator circuit for receiving a shaper voltage from the PCCT signal chain, the discriminator circuit outputting a digital signal indicative of one of a range of voltages within which the shaper voltage falls; a digital-to-analog converter ("DAC") connected to receive the digital signal output from the discriminator circuit, the DAC converting the received digital signal to a corresponding active reference voltage; and a feedback circuit that injects a cancellation current proportional to a difference between the shaper voltage and the active reference voltage at a specific node of the PCCT signal chain.

Example 2 provides the circuitry of example 1, wherein the difference between the shaper voltage and the active reference voltage is computed by a linear amplifier.

Example 3 provides the circuitry of example 2, wherein a signal output from the linear amplifier is applied to an input of a low-pass filter.

Example 4 provides the circuitry of example 3, further comprising a transconductor connected to receive a filtered voltage signal output from the low pass filter, convert the filtered voltage signal to a current signal, and feed the current signal back to an input of the PCCT signal chain.

Example 5 provides the circuitry of any of examples 2-4, wherein the low pass filter functions as an integrator.

Example 6 provides the circuitry of any of examples 1-5, wherein the BLR circuit is a delta modulator.

Example 7 provides the circuitry of any of examples 1-6, wherein the difference between the shaper voltage and the active reference voltage is computed by a comparator.

Example 8 provides the circuitry of example 7, wherein the output of the comparator is applied to the input of a low-pass filter.

Example 9 provides the circuitry of any of examples 6-8, wherein the BLR circuit is clocked.

Example 10 provides the circuitry of example 9, wherein chopper stabilization is applied to null out an offset of the comparator.

Example 11 provides the circuitry of any of examples 1-10, wherein the cancellation current is injected at an input of the PCCT signal chain.

Example 12 provides a method for implementing baseline restoration ("BLR") in connection with a photo-counting computed tomography ("PCCT") signal chain, the method comprising receiving a shaper voltage from the PCCT signal chain and generating a digital signal indicative of one of a range of voltages within which the shaper voltage falls; converting the received digital signal to a corresponding active reference voltage; and injecting a cancellation current proportional to a difference between the shaper voltage and the active reference voltage at the input of the PCCT signal chain.

Example 13 provides the method of example 12, wherein the difference between the shaper voltage and the active reference voltage is computed by a linear amplifier.

Example 14 provides the method of any of examples 12-13, further comprising applying a signal output from the linear amplifier to an input of a low-pass filter.

Example 15 provides the method of any of examples 12-14, further comprising filtering the comparator voltage;

converting the filtered comparator voltage to a current signal; and feeding the current signal back to an input of the PCCT signal chain.

Example 16 provides the method of example 15, wherein the filtering, converting, and feeding effectively functions as a delta modulator.

Example 17 provides the method of any of examples 14-16, wherein the low pass filter functions as an integrator.

Example 18 provides the method of any of examples 12-17, wherein the difference between the shaper voltage and the active reference voltage is computed by a comparator.

Example 19 provides the method of example 18, wherein a signal output from the comparator is applied to an input of a low-pass filter.

Example 20 provides the method of any of examples 16-19, further comprising clocking a circuit for implementing the BLR.

Example 21 provides the method of any of examples 12-20, further comprising applying chopper stabilization to null out an offset of an input comparator.

Example 22 provides the method of any of examples 12-21, wherein the cancellation current is injected at an input of the PCCT signal chain.

Example 23 provides an apparatus for performing baseline restoration ("BLR") for a photon-counting computed tomography ("PCCT") signal chain, the apparatus comprising first circuitry for receiving a shaper voltage from the PCCT signal chain and outputting a digital signal indicative of a detected level of the shaper voltage; second circuitry for converting the digital signal output from the first circuitry to an active reference voltage; and third circuitry for injecting a cancellation current proportional to a difference between the shaper voltage and the active reference voltage at an input of the PCCT signal chain, wherein the third circuitry comprises at least one of a linear amplifier and a comparator for outputting the difference between the shaper voltage and the active reference voltage.

Example 24 provides the apparatus of example 23, wherein a signal output from the linear amplifier is applied to an input of a low-pass filter.

Example 25 provides the apparatus of example 24, further comprising a transconductor connected to receive a filtered voltage signal output from the low pass filter, convert the filtered voltage signal to a current signal, and feed the current signal back to an input of the PCCT signal chain.

Example 26 provides the apparatus of any of examples 24-25, wherein the low pass filter functions as an integrator.

Example 27 provides the apparatus of any of examples 23-26, wherein the BLR is implemented using a delta modulator.

It should be noted that all of the specifications, dimensions, and relationships outlined herein (e.g., the number of elements, operations, steps, etc.) have only been offered for purposes of example and teaching only. Such information may be varied considerably without departing from the spirit of the present disclosure, or the scope of the appended claims. The specifications apply only to one non-limiting example and, accordingly, they should be construed as such. In the foregoing description, exemplary embodiments have been described with reference to particular component arrangements. Various modifications and changes may be made to such embodiments without departing from the scope of the appended claims. The description and drawings are, accordingly, to be regarded in an illustrative rather than in a restrictive sense.

Note that with the numerous examples provided herein, interaction may be described in terms of two, three, four, or more electrical components. However, this has been done for purposes of clarity and example only. It should be appreciated that the system may be consolidated in any suitable manner. Along similar design alternatives, any of the illustrated components, modules, and elements of the FIGURES may be combined in various possible configurations, all of which are clearly within the broad scope of this Specification. In certain cases, it may be easier to describe one or more of the functionalities of a given set of flows by only referencing a limited number of electrical elements. It should be appreciated that the electrical circuits of the FIGURES and its teachings are readily scalable and may accommodate a large number of components, as well as more complicated/sophisticated arrangements and configurations. Accordingly, the examples provided should not limit the scope or inhibit the broad teachings of the electrical circuits as potentially applied to myriad other architectures.

It should also be noted that in this Specification, references to various features (e.g., elements, structures, modules, components, steps, operations, characteristics, etc.) included in "one embodiment", "exemplary embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

It should also be noted that the functions related to circuit architectures illustrate only some of the possible circuit architecture functions that may be executed by, or within, systems illustrated in the FIGURES. Some of these operations may be deleted or removed where appropriate, or these operations may be modified or changed considerably without departing from the scope of the present disclosure. In addition, the timing of these operations may be altered considerably. The preceding operational flows have been offered for purposes of example and discussion. Substantial flexibility is provided by embodiments described herein in that any suitable arrangements, chronologies, configurations, and timing mechanisms may be provided without departing from the teachings of the present disclosure.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

Note that all optional features of the device and system described above may also be implemented with respect to the method or process described herein and specifics in the examples may be used anywhere in one or more embodiments.

The 'means for' in these instances (above) may include (but is not limited to) using any suitable component discussed herein, along with any suitable software, circuitry, hub, computer code, logic, algorithms, hardware, controller, interface, link, bus, communication pathway, etc.

Note that with the example provided above, as well as numerous other examples provided herein, interaction may be described in terms of two, three, or four network elements. However, this has been done for purposes of clarity and example only. In certain cases, it may be easier to describe one or more of the functionalities of a given set of flows by only referencing a limited number of network elements. It should be appreciated that topologies illustrated in and described with reference to the accompanying FIGURES (and their teachings) are readily scalable and may accommodate a large number of components, as well as more complicated/sophisticated arrangements and configurations. Accordingly, the examples provided should not limit the scope or inhibit the broad teachings of the illustrated topologies as potentially applied to myriad other architectures.

It is also important to note that the steps in the preceding flow diagrams illustrate only some of the possible signaling scenarios and patterns that may be executed by, or within, communication systems shown in the FIGURES. Some of these steps may be deleted or removed where appropriate, or these steps may be modified or changed considerably without departing from the scope of the present disclosure. In addition, a number of these operations have been described as being executed concurrently with, or in parallel to, one or more additional operations. However, the timing of these operations may be altered considerably. The preceding operational flows have been offered for purposes of example and discussion. Substantial flexibility is provided by communication systems shown in the FIGURES in that any suitable arrangements, chronologies, configurations, and timing mechanisms may be provided without departing from the teachings of the present disclosure.

Although the present disclosure has been described in detail with reference to particular arrangements and configurations, these example configurations and arrangements may be changed significantly without departing from the scope of the present disclosure. For example, although the present disclosure has been described with reference to particular communication exchanges, embodiments described herein may be applicable to other architectures.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 142 as it exists on the date of the filing hereof unless the words "means for" or "step for" are specifically used in the particular claims; and (b) does not intend, by any statement in the specification, to limit this disclosure in any way that is not otherwise reflected in the appended claims.

What is claimed is:

1. Circuitry to implement baseline restoration (BLR) for a photon-counting computed tomography (PCCT) signal chain, the circuitry comprising:
    a multi-level discriminator circuit configured to receive a shaper voltage from the PCCT signal chain, the multi-level discriminator circuit outputting a digital signal indicative of one of a range of voltages within which the shaper voltage falls;
    a digital-to-analog converter (DAC) connected to receive the digital signal output from the multi-level discriminator circuit, the DAC configured to convert the received digital signal to a corresponding active reference voltage; and
    a feedback circuit configured to inject a cancellation current proportional to a difference between the shaper voltage and the active reference voltage at a specific node of the PCCT signal chain.

2. The circuitry of claim 1, wherein the difference between the shaper voltage and the active reference voltage is computed by a linear amplifier.

3. The circuitry of claim 2, wherein a signal output from the linear amplifier is applied to an input of a low-pass filter.

4. The circuitry of claim 3, further comprising a transconductor connected to receive a filtered voltage signal output from the low pass filter, convert the filtered voltage signal to a current signal, and feed the current signal back to an input of the PCCT signal chain.

5. The circuitry of claim 1, further comprising a baseline restoration (BLR) circuit that is a delta modulator.

6. The circuitry of claim 5, wherein the BLR circuit is clocked.

7. The circuitry of claim 1, wherein the difference between the shaper voltage and the active reference voltage is computed by a comparator and wherein the output of the comparator is applied to the input of a low-pass filter.

8. The circuitry of claim 7, wherein chopper stabilization is applied to null out an offset of the comparator.

9. A method for implementing baseline restoration ("BLR") for a photo-counting computed tomography ("PCCT") signal chain, the method comprising:
    receiving a shaper voltage from the PCCT signal chain;
    generating a digital signal indicative of one of a range of voltages within which the shaper voltage falls;
    converting the digital signal to a corresponding active reference voltage; and
    injecting a cancellation current proportional to a difference between the shaper voltage and the active reference voltage at the input of the PCCT signal chain.

10. The method of claim 9, wherein the difference between the shaper voltage and the active reference voltage is computed by a linear amplifier.

11. The method of claim 9, further comprising applying a signal output from the linear amplifier to an input of a low-pass filter, wherein the low-pass filter functions as an integrator.

12. The method of claim 9, further comprising:
    filtering the comparator voltage;
    converting the filtered comparator voltage to a current signal; and
    feeding the current signal back to an input of the PCCT signal chain.

13. The method of claim 12, wherein the filtering, converting, and feeding effectively functions as a delta modulator.

14. The method of claim 9, wherein the difference between the shaper voltage and the active reference voltage is computed by a comparator.

15. The method of claim 9, further comprising clocking a circuit for implementing the BLR.

16. The method of claim 9, further comprising applying chopper stabilization to null out an offset of an input comparator.

17. An apparatus for baseline restoration (BLR) for a photon-counting computed tomography (PCCT) signal chain, the apparatus comprising:
    first circuitry configured to receive a shaper voltage from the PCCT signal chain and further configured to output a digital signal indicative of a detected level of the shaper voltage;
    second circuitry configured to convert the digital signal output from the first circuitry to an active reference voltage; and
    third circuitry configured to inject a cancellation current proportional to a difference between the shaper voltage and the active reference voltage at an input of the PCCT signal chain, wherein the third circuitry comprises at least one of a linear amplifier and a comparator configured to output the difference between the shaper voltage and the active reference voltage.

18. The apparatus of claim 17, wherein a signal output from the linear amplifier is applied to an input of a low-pass filter.

19. The apparatus of claim 17, further comprising a transconductor connected to receive a filtered voltage signal output from the low pass filter, convert the filtered voltage signal to a current signal, and feed the current signal back to the input of the PCCT signal chain.

20. The apparatus of claim 17, wherein the output of the comparator is applied to the input of a low-pass filter and wherein chopper stabilization is applied to null out an offset of the comparator.

* * * * *